(12) United States Patent
Da Silva Pinto et al.

(10) Patent No.: US 8,673,971 B2
(45) Date of Patent: Mar. 18, 2014

(54) DERIVATIVES OF 4-NEROLIDYLCATECHOL, PHARMACEUTICAL COMPOSITIONS COMPRISING THEM AND PROCESS FOR PRODUCING THE SAME

(75) Inventors: Ana Cristina Da Silva Pinto, Manaus-AM (BR); Márcia Rúbia Silva Melo, Manaus-AM (BR); Valter Ferreira De Andrade Neto, Manaus-AM (BR); Francisco Célio Maia Chaves, Manaus-AM (BR); Pedro Paulo Ribeiro Vieira, Manaus-AM (BR); Adrian Martin Pohlit, Manaus-AM (BR)

(73) Assignee: Instituto Nacional de Pesquisa de Amazonia INPA, Manaus (BR)

( * ) Notice: Subject to any disclaimer, the term of this patent is extended or adjusted under 35 U.S.C. 154(b) by 233 days.

(21) Appl. No.: 12/810,661

(22) PCT Filed: Dec. 28, 2007

(86) PCT No.: PCT/BR2007/000373
§ 371 (c)(1),
(2), (4) Date: Feb. 25, 2011

(87) PCT Pub. No.: WO2009/082795
PCT Pub. Date: Jul. 9, 2009

(65) Prior Publication Data
US 2011/0136901 A1    Jun. 9, 2011

(51) Int. Cl.
*A61K 31/335* (2006.01)
*A61K 31/235* (2006.01)
*A61K 31/19* (2006.01)
*A61K 31/05* (2006.01)
*C07D 303/00* (2006.01)
*C07C 69/76* (2006.01)
*C07C 63/64* (2006.01)
*C07C 39/00* (2006.01)

(52) U.S. Cl.
USPC ........... 514/475; 514/544; 514/570; 514/733; 549/513; 560/104; 562/495; 568/716

(58) Field of Classification Search
USPC ................ 514/475, 544, 570, 733; 549/513; 560/104; 562/495; 568/716
See application file for complete search history.

(56) References Cited

U.S. PATENT DOCUMENTS

2006/0062858 A1* 3/2006 de Moraes Barros et al. ............................ 424/725

* cited by examiner

*Primary Examiner* — Taylor Victor Oh
(74) *Attorney, Agent, or Firm* — Laurence P. Colton; Smith Risley Tempel Santos LLC

(57) ABSTRACT

The present invention discloses 4-nerolidylcatechol and its derivatives isolated from South American/Amazon plants (*Pothomorphe* species) and their potential use as therapeutical agent for treatment of malarial symptoms, including malarial patients resistant to traditional drugs. The present invention also discloses a method for producing 4-nerolidylcatechol and their derivatives.

14 Claims, No Drawings

DERIVATIVES OF 4-NEROLIDYLCATECHOL, PHARMACEUTICAL COMPOSITIONS COMPRISING THEM AND PROCESS FOR PRODUCING THE SAME

FIELD OF THE INVENTION

The present invention discloses 4-nerolidylcatechol derivatives and their use in pharmaceutical compositions, as composition for the treatment of malaria in general. The present invention also discloses a method for producing 4-nerolidylcatechol derivatives.

BACKGROUND OF THE INVENTION

Malaria

Malaria is the main cause of economic loss and high morbidity in the world today. It is an infectious disease caused by protozoan parasites and continues to be endemic at tropical regions, such as Amazon.

In the Brazilian Amazon, 1.6 million positive plates in a total of 8 million diagnostic tests for malaria were registered. The lack of an effective vaccine and the increasing expansion of strains of *Plasmodium falciparum* presenting resistance towards commonly used, low cost antimalarials make control of this disease difficult. As a result, the WHO has been promoting research on natural product based drugs for treatment of disease and many plant species have been evaluated for antimalarial activity [Weninger, 2004].

The triage of useful and effective plants is at the heart of traditional medicinal knowledge and is an extremely important source of therapeutic compounds in use today. Important semi-synthetic, low cost, highly effective antimalarial drugs such as the quinolines (chloroquine, mefloquine and primaquine) and artemisinin derivatives (sodium artesunate, arteether, artemether) owe their initial discovery to the isolation and structural identification of antimalarial natural products (quinine and artemisinin) from traditionally used antimalarial plant species (*Cinchona* spp. and *Artemisia annua*) [Rosenthal (2003)].

Recent studies on traditionally used antimalarial remedies have revealed plants which produce indole and isoquinoline alkaloids, sesqui-, di- and triterpenes, flavonoids and other substances presenting proven in vitro activity against *P. falciparum* [Frederich (1999)]

There is a high risk of contracting highly chloroquine-resistant falciparum malaria in the Amazon, especially at the "legal Amazon" (Amazon, Mato Grosso and Maranhao), but it also exists in adjacent parts of Colombia, Peru, Bolivia and Venezuela. For those patients using chloroquine, around 20% of treatment failure rates have been reported in some areas of Amazon. Furthermore, sulfadoxine pyramethamine (a second-line antimalarial drug) resistance has been reported in Colombia, Peru and Venezuela.

Studies on the macromolecular profiles of these parasites in association with analysis of genetic resistance markers should contribute to elucidate the possible mechanisms of resistance of the parasites to the natural products tested as well as aid in the discovery of new targets and/or new mechanisms of action for antimalarial chemotherapy [Mu (2007)].

Medicinal Plants

Species of the *Pothomorphe* genus (*P. umbellata* and *P. petalta*) are commonly found in Brazil. *Pothomorphe peltata* (L.) Miguel is a small tree, around 1 to 2 m height and can be found at Central and South America. [Missouri Botanical Garden (2002)]. It is known by many popular names, as caapeba, pariparoba, caapeba-do-Norte, malvarisco, aguaxima, among others. This species is commonly used in traditional medicine to treat patients with malaria [Bastos (1998)], liver diseases and ulcers [Desmarchelier (1997)], headaches, hepatite and conjuntivite [Egg (1999)], erysipelas, leishmaniose [Mors (2000)], burns [Di Stasi (2002)]. It is also used as antiinflamatory, diuretic, abortive, stimulating [Jardim (2002)], feed [Egg (1999)], sudoriferous and tonic [Rodrigues (1989)]

The extract of *P. umbellata* roots and 4-nerolidylcatechol compound, a catechol prenylated found in both species, can be used as cosmetics and pharmaceutical formulations. Many models were tested to evaluate the antioxidant and photo protection activity in vitro and in vivo of this compound.

The hydroalcoholic extract of roots and the compound 4-nerolidylcatechol were tested in gel formulations to establish the chemical stability and the factor of solar protection using irradiation with UVB lamps. (SILVA et al., 2005). ROPKE (2002, 2003) studied the cutaneous permeation and the effects of the topical application of formulations containing 4-nerolidylcatechol (gel, cream-gel and creams). This study involved in vivo analyses about the chronic and acute problems within the UV radiation. It showed that the gel was the most effective vehicle to be used on the skin. In 2002, a Brazilian patent protected the right to use the *P. umbellata* extract as a topical cosmetic and pharmaceutical formulation to prevent/oppose the effects of photo oxidatives on the skin, skin aging and/or skin cancer (INPI, 2004).

In order to allow the use of 4-nerolidylcatechol in pharmaceutical formulations, some studies were done about stability, solubility and bioavailability of complexes of 4-nerolidylcatechol (which has low water solubility) containing hydroxypropyl-β-ciclodextrines (HP-β-CD). The increase of hydroxypropyl-β-ciclodextrines concentration lead to an increase of 4-nerolidylcatechol water solubility (VALERIANO et al., 2005).

In vivo studies showed that the hydroalcoholic extract of roots having 25.4% of 4-nerolidylcatechol can be used as a protector agent (topical use) against the damage caused by the UV irradiation (ROPKE et al., 2003, 2005).

Besides, the ethanolic extract of the *P. umbellata* roots showed a greater inhibitory effect of metaloproteases (MMPs—enzymes which regulates the exposition to radiation UV) in vivo than the 4-nerolidylcatechol compound (ROPKE et al., 2006).

Many studies disclose the properties of *P. petalta* and *P. umbellata* as antioxidants, as well as the alkylcatechol 4-nerolidylcatechol. In vitro studies showed that *P. umbellata* leaf methanol extract had antioxidant activity (AGBOR et al., 2005).

Another example of antioxidant activity given by leaf methanol extracts could be seen analyzing hydroperoxide luminescence of liver homogenates (DESMARCHELIER et al., 1997a).

The capability to capture the peroxyl radical was determined through the total reactive antioxidant potential (TRAP) and total antioxidant reactivity (TAR) using 2,2-azobis(2-amidinopropano) (ABAP) to modulate the luminol luminescence. This capability was as high for the leaf methanol extracts as for the 4-nerolidylcatechol compound. The latter also exhibited hydroxyl inhibition mediated by DNA damage induced by Fe (II) salts. (DESMARCHELIER et al., 1997b; BARROS et al., 1996).

PASQUALOTO et al. (2001) found evidence that the antioxidant activity of 4-nerolidylcatechol is associated with the oxidation of its alkyl side chain. This was observed in alkenyl resorcinol compounds, where the electrostatic and lipophilic potentials were measured at the aromatic rings and lateral chains. 4-nerolidylcatechol presented in vitro antioxidant activity 20 times greater than α-tocoferol, using tests based on co-oxidation of substrate (β-carotene, linoleic acid) and simultaneous lipoperoxidation can be seen in rat brain homogenates.

The water-alcohol extract of roots showed a greater antioxidant effect compared to the leaves and stamen extracts (DE FREITAS, 1999).

OBJECTS OF THE INVENTION

It is an objective of the 4-nerolidylcathecol derivative invention according to general formulas (I) and/or (II):

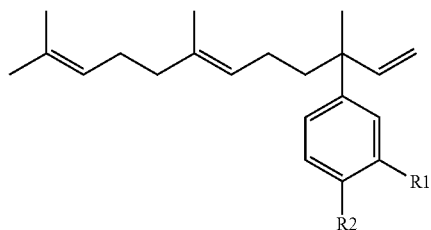
(I)

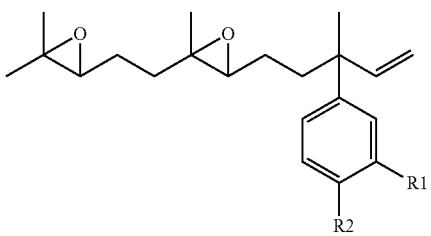
(II)

wherein:

R1 and R2 are, independently, chosen from the group comprising OH, OC(=O)C$_6$H$_5$, acetate, OCH$_2$(C$_6$H$_5$) and mixtures thereof; and Its salts, solvates, hydrates and/or isomers.

It is a further object of the invention a pharmaceutical compositions comprising:

a) 4-nerolidylcatechol derivatives according to general formulas (I) and/or (II):

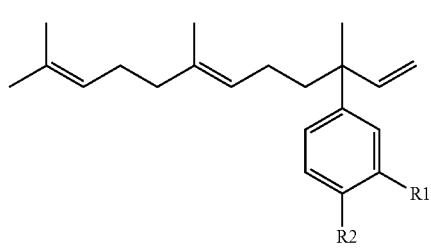
(I)

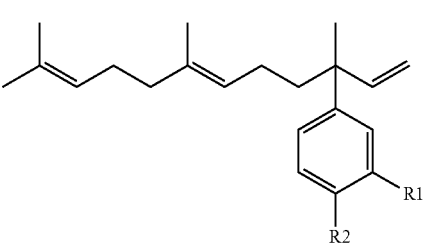
(I)

(II)

wherein:

R1 and R2 are, independently, chosen from the group comprising OH, OC(=O)C$_6$H$_5$, acetate, OCH$_2$(C$_6$H$_5$), OCH$_3$, and mixtures thereof; and Its salts, solvates, hydrates and/or isomers; and b) a pharmaceutically acceptable vehicle In a preferred embodiment, said composition has antimalarial activity.

It is a further object of the present invention a method for producing 4-nerolidylcatechol derivatives comprising the steps of:

a) isolating 4-nerolidylcathecol from a plant material;

b) performing at least one of the following reactions:
   Methylation;
   Benzylation;
   Benzoylation;
   Epoxidation;
   Acetylation;

DETAILED DESCRIPTION OF THE INVENTION

The following examples are illustrative of the present invention and are by no means intended to limit the scope of the present invention.

As used here, the expression "pharmaceutical compositions" should be understood as any and all compositions with an active principle, prophylactic or healing to maintain or restoring the homeostase, formulated for topical, oral, parenteral, intranasal, intravenous, intramuscular, subcutaneous or intraocular administration and the like. The meaning of the expression "active principle" comprises all or any compounds of general formula (I) and (II) and their salts, solvates, hydrates and/or isomers.

4-Nerolidylcathecol Derivatives

The 4-nerolidylcathecol derivatives disclosed herein are compounds having structures according to general formulas (I) and/or (II) below:

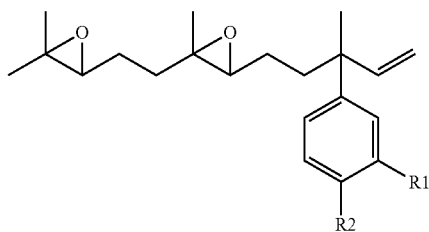

(II)

wherein:

R1 and R2 are, independently, chosen from the group comprising H, OH, $C_1$-$C_8$ alkyl, $C_1$-$C_5$ acolxy, OC(=O)$C_6H_5$, formate, acetate, propionate, butanoate, pentanoate, OCH$_2$ ($C_6H_5$) and mixtures thereof.

In a preferred embodiment, the following structures are synthesized:

Compound 1—General formula (I) wherein R1 is OCOC$_6$H$_5$ and R2 is OCOC$_6$H$_5$.

Compound 2—General formula (I) wherein R1 is, OCH$_2$(C$_6$H$_5$) and R2 is OCH$_2$(C$_6$H$_5$).

Compound 3—General formula (I) wherein R1 is, OCH$_2$(C$_6$H$_5$) and R2 is OH.

Compound 4—General formula (I) wherein R1 is and R2 is OCH$_2$(C$_6$H$_5$).

Compound 5—General formula (I) wherein R1 is, acetate and R2 is acetate.

Compound 6—General formula (II) wherein R1 is acetate and R2 is acetate.

Compound 7—General formula (I) wherein R1 is OCH$_3$ and R2 is OH.

Compound 8—General formula (I) wherein R1 is OH and R2 is OCH$_3$.

4-Nerolidylcathecol

The starting compound 4-nerolidylcathecol can be obtained from plant extracts of *Pothomorphe* (*P. umbellata* e *P. peltata*). The extract of *Pothomorphe* can be obtained through several methods disclosed in the art. The starting plant material can be any part of the plant (leaves, roots, stems and inflorescence). The most common methods are:

a) Cold Maceration—known amounts of plant material are put in contact with a solvent, which is changed every 48 hours, filtered and concentrated in rotary evaporator at low temperatures. Solvents such as chloroform, methanol and chloroform:methanol 1:1 were evaluated.

b) Soxhlet—known amounts of plant material are put into filter-paper cartridges and the chosen solvent is added (about 400 mL). Several solvents were tested, such as chloroform, ethyl acetate, ethanol, hexane, methanol, and mixtures chloroform:ethanol 1:1 and chloroform:methanol 1:1, as well as nitrogen atmosphere, varying the extraction time.

c) Ultrasound—known amounts of plant material (ca. 5 g) were weighed and put into a flask with 150 mL of a chosen solvent such as chloroform, ethyl acetate, acetone, hexane, methanol, and mixtures chloroform:ethanol 1:1, for 15 minutes under ultrasound, for a total of 3 extractions. The extract is filtered, concentrated in rotary-evaporator and lyophilized.

The most preferred method is the Ultrasound method, due to its speed and efficiency. After the extracts were produced, the 4-nerolidylcathecol was isolated from them.

Synthesis of the Semi-Synthetic Derivatives

All the synthesized derivatives were characterized by spectroscopic methods such as (NMR $_1$H, $_{13}$C, Cosy, HMBC e HSQC). The semi-synthetic derivatives were prepared from the natural product 4-nerolidylcathecol, through several reactions such as:

1) Methylation reactions—using methyl iodide in potassium carbonate and dichloromethane and/or diazomethane.

2) Benzylation reactions—using benzyl bromide or chloride, dimethylformamide in double-boiling for 20-30 min. The reaction remained under stirring in room temperature for 18 h.

3) Benzoylation reactions—using pyridine or triethylamine in benzoyl chloride, under N$_2$ atmosphere and stirring for 1-24 hours.

4) Epoxidation reactions—using meta-chloroperbenzoic acid in dichloromethane at 0° C., under N$_2$ atmosphere and stirring for 4.5-72 hours.

5) Acetylation reactions—using acetic anhydride and pyridine, under N$_2$ atmosphere and stirring for 4.5-72 hours.

The yields for each reaction vary from 10 to 80%, and the derivatives were isolated by chromatography.

Example 1

Isolation of 4-Nerolidylcathecol 19.5 g of Chloroform:ethanol (1:1) extract from roots of *P. peltata* (prepared by ultrasound method) were passed through a silica-gel chromatographic column (Ø=5.0 cm; h=38 cm), using chloroform:ethanol (9:1) as mobile phase and methanol. 14 fractions were obtained and were compared with a standard sample with 4-nerolidylcathecol.

The fractions containing 4-nerolidylcathecol were then purified with preparative TLC using as elution system a mixture of chloroform:ethanol (85:15). The final yield of 4-nerolidylcathecol was 8.6 g (44%) and a total yield of 5.7% based on the dry and ground root (w/w).

Example 2

Semi-Synthesis of 4-Nerolidylcathecol Derivatives 2.1 Benzoylation Reaction 4-nerolidylcathecol was solubilized in pyridine under nitrogen atmosphere and stirring, followed by drop addition of benzoyl chloride. The solution was heated for 20 min at 110° C. under stirring. The reaction remained at room temperature under agitation for 139 h. The post-reaction protocol began with the addition of 5 mL of cold water to the medium, extracting with chloroform (2×5 mL) and 3×5 mL of water, in an alternate fashion.

The chloroform phase was washed with HCl 0.1N (2×5 mL), diluted NaHCO$_3$ (2×5 mL), water (5 mL) and saturated NaCl (2×5 mL). The solution of CHCl$_3$ was dried with anhydrous sodium sulphate, filtered and the solvent removed by a rotary evaporator.

The product was purified by column chromatography, yielding a mixture of monobenzoylated derivatives and separated by preparative thin layer chromatography.

2.2 Benzylation Reaction 4-nerolidylcathecol was solubilized in DMF under Nitrogen atmosphere and stirring, followed by addition of potassium carbonate and benzyl chloride. The reaction remained at room temperature under agitation for 158 h. 5 mL of water was added, extracted with 20 mL of chloroform. The organic phase was washed with water (5 mL), saturated sodium chloride solution (6.5 mL) and dried with MgSO4, filtered and concentrated via rotary evaporator.

The product was purified by column chromatography, yielding a mixture of monobenzylated derivatives and separated by preparative thin layer chromatography.

2.3 Acetylation Reaction 4-nerolidylcathecol was added to acetic anhydride and pyridine, under nitrogen atmosphere and stirring for 24 hours. The post-reaction protocol began with the addition of 3 mL of water to the reaction, extraction with chloroform (5 mL).

The chloroform phase was washed with HCl 0.1N (2×3 mL), saturated solution of $NaHCO_3$ (2×3 mL), water (3 mL) and saturated NaCl (2×3 mL). The solution of $CHCl_3$ was dried with anhydrous sodium sulphate, filtered and the solvent removed by a rotary evaporator.

The product was purified by column chromatography, yielding a diacetylated derivative.

2.4 Epoxidation Reaction of the Diacetylated Reaction

The diacetylated 4-nerolidylcathecol derivative from the previous item was dissolved in dichloromethane with 1.2% M of meta-chloroperbenzoic acid (m-CPBA) in dichloromethane. The flask remained, in the first two hours, in a NaCl ice bath at −5° C. and then at room temperature, under nitrogen atmosphere and stirring for 11 days.

After this period, the reaction was treated with aqueous $Na_2S_2O_3$ (to neutralizing the oxidative power), followed by aqueous $NaHCO_3$ (for neutralization of acids). The solution was filtered and extracted with chloroform. The organic phases were washed with water and dried with anhydrous $NaSO_4$. The product was purified by flash chromatography.

2.5 Methylation Reaction 4-nerolidylcathecol (410 mg) was treated with diazomethane (10 mL) at room temperature. The solvent was removed by rotary evaporator and the product was purified by column chromatography, obtaining monomethylated derivatives and separated by preparative thin layer chromatography.

Example 3

Biological Assays

In Vitro Test to Evaluate the Growth Inhibition of *P. falciparum*

Initially, the parasites were sincronized to trophozoite stage with the ring shape, using the sorbitol treatment (LAMBROS, VANDERBERG, 1979). Stock solutions of each extract, pure compound or derivative were done in DMSO or ethanol with an initial concentration of 50 mg/mL for the extracts and 10 mg/mL for pure substances. A volume of 20 μL of each stock solution was transferred to microtubes containing growth medium RPMI complete.

Aliquots of 150 μL were added to microplates containing 96 wells each. To those wells were added 100 μL of parasited blood (final volume of 250 μL), 1% of parasitemy and initial concentration of 500 μg/mL for the extracts and 50 μg/mL for the pure substances. Control was prepared exchanging the stock solution to DMSO or ethanol (negative control) or antimalarial chloroquine, quinine or arthemisinine (positive control).

The plates were left to rest without direct light at 37° C., 5% of $CO_2$ atmosphere, 5% of $O_2$ and 90% of $N_2$ and the antiplasmodial activity was evaluated after 48 h for extracts and 24 h for pure substances or semi-synthetic derivatives. The parasitemy of each well was determined by the colored blood smear exam using the Panotic method in an optic microscope, with lens of 100 times.

The parasitemy was expressed in percentage of viable erythrocites shapes observed during the counting of 3000 red blood cell and the inhibition was expressed in percentage. All the clinical studies were made in triplicate. The concentration of the samples required to reduce in 50% the growth of the parasite ($CL_{50}$) were calculated by linear regression using dose-response curves.

Results

The benzoylated derivatives, monobenzoylated, benzylated, monobenzylated, epoxide and monomethylated presented growth inhibition potential of stocks K1 of *P. falciparum* in vitro, comparable to the natural substance and standard substance.

The invention claimed is:

1. A compound having a structure according to formula (I):

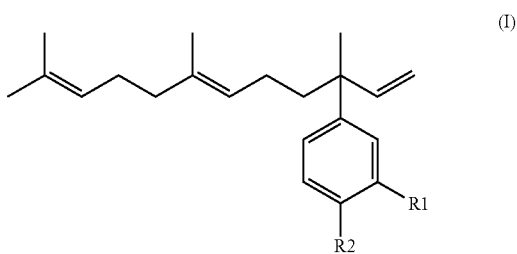

(I)

and its salts,
wherein:
R1 and R2 are selected from the group consisting of:
  R1 is $OCOC_6H_5$ and R2 is $OCOC_6H_5$;
  R1 is $OCH_2(C_6H_5)$ and R2 is $OCH_2(C_6H_5)$;
  R1 is $OCH_2(C_6H_5)$ and R2 is OH;
  R1 is $O(C=O)CH_3$ and R2 is $O(C=O)CH_3$;
  R1 is $OCH_3$ and R2 is OH; and
  R1 is OH and R2 is $OCH_3$.

2. A pharmaceutical composition comprising:
a) a compound according to formula (I):

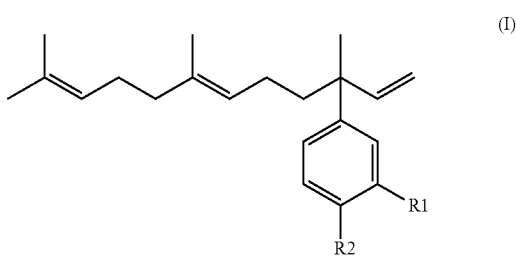

(I)

and its salts; and
a pharmaceutically acceptable vehicle,
wherein:
R1 and R2 selected from the group consisting of:
  R1 is $OCOC_6H_5$ and R2 is $OCOC_6H_5$;
  R1 is $OCH_2(C_6H_5)$ and R2 is $OCH_2(C_6H_5)$;
  R1 is $OCH_2(C_6H_5)$ and R2 is OH;
  R1 is $O(C=O)CH_3$ and R2 is $O(C=O)CH_3$;
  R1 is $OCH_3$ and R2 is OH; and
  R1 is OH and R2 is $OCH_3$.

3. A compound having a structure according to formula (II):

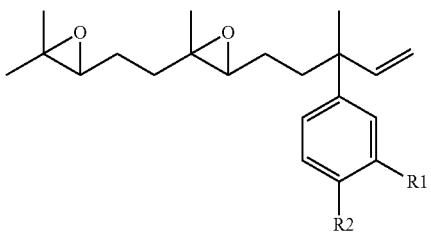

and its salts,
wherein R1 and R2 are OC(=O)CH$_3$.

4. A pharmaceutical composition comprising:
a compound according to formula (II):

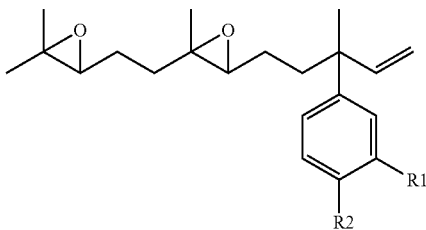

and its salts; and
a pharmaceutically acceptable vehicle,
wherein R1 and R2 are OC(=O)CH$_3$.

5. A process for producing the compound of claim 3, comprising the steps of:
 a) isolating 4-nerolidylcathecol from a plant material; and
 b) performing at least one of the following reactions on the 4-nerolidylcathecol:
  Methylation;
  Benzylation;
  Benzoylation;
  Epoxidation; or
  Acetylation.

6. The process according to claim 5, further comprising obtaining the 4-nerolidylcathecol from plant extracts of a plant selected from the genus *Pothomorphe*.

7. The process according to claim 6, further comprising selecting the plant from the group consisting of *P. umbellate, P. peltata*, and combinations thereof.

8. The process according to claim 6, wherein the extract of *Pothomorphe* is obtained from the group consisting of leaves, roots, stems, inflorescence, and combinations thereof.

9. The process according to claim 6, further comprising a method used to obtain the plant extracts chosen from the group consisting of cold maceration, soxhlet, and ultrasound.

10. The process according to claim 9, wherein the method used to obtain the plant extracts is ultrasound.

11. The process of production, according to claim 5, further comprising isolating the 4-nerolidylcathecol by chromatography.

12. A method for inhibiting the growth of parasites by contacting the parasites with an anti-parasitically effective amount of a pharmaceutical composition comprising:
 a) a compound according to formulas (I) and/or (II):

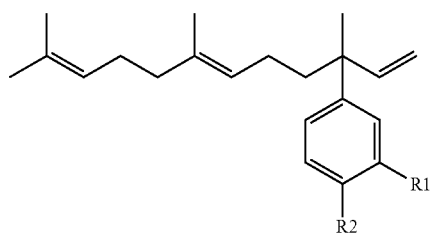

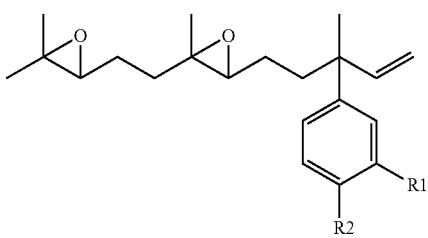

or its salts; and
 b) a pharmaceutically acceptable vehicle,
 wherein when the compound has a structure according to formula (I), R1 and R2 are selected from the group consisting of:
  R1 is OCOC$_6$H$_5$ and R2 is OCOC$_6$H$_5$;
  R1 is OCH$_2$(C$_6$H$_5$) and R2 is OCH$_2$(C$_6$H$_5$);
  R1 is OCH$_2$(C$_6$H$_5$) and R2 is OH;
  R1 is O(C=O)CH$_3$ and R2 is O(C=O)CH$_3$;
  R1 is OCH$_3$ and R2 is OH; and
  R1 is OH and R2 is OCH$_3$, and
 wherein when the compound has a structure according to formula (II), R1 is O(C=O)CH$_3$ and R2 is O(C=O)CH$_3$.

13. The method according to claim 12, wherein the parasites are from the genus *Plasmodium*.

14. The method according to claim 12, wherein the parasites are *Plasmodium falciparum*.

* * * * *